United States Patent [19]
Melchers et al.

[11] Patent Number: 5,994,625
[45] Date of Patent: Nov. 30, 1999

[54] ANTIFUNGAL CHITIN BINDING PROTEINS AND DNA CODING THEREFOR

[75] Inventors: Leo Sjoerd Melchers, Leiden; Marianne Beatrix Sela-Buurlage, Amersfoort; Alexandra Aleida Bres-Vloemans; Anne Silene Ponstein, both of Leiden; Marion Apotheker-De Groot, Haarlem; Bernardus Johannes Clemens Cornelissen, Warmond, all of Netherlands

[73] Assignee: Mogen International N.V., CB Leiden, Netherlands

[21] Appl. No.: 08/935,886

[22] Filed: Sep. 23, 1997

Related U.S. Application Data

[63] Continuation of application No. 08/411,640, filed as application No. PCT/EP93/02790, Oct. 5, 1993, abandoned.

[30] Foreign Application Priority Data

Oct. 5, 1992 [EP] European Pat. Off. .............. 92203071
May 13, 1993 [EP] European Pat. Off. .............. 93201370

[51] Int. Cl.$^6$ .............................. A01H 5/00; C12N 15/29; C12N 15/82; C12N 15/84
[52] U.S. Cl. .......................... 800/279; 800/265; 800/268; 800/294; 800/298; 800/301; 435/69.1; 435/200; 435/209; 435/252.2; 435/320.1; 435/418; 435/419; 435/421; 435/468; 435/469; 536/23.6
[58] Field of Search .......................... 536/23.6; 435/69.1, 435/70.1, 172.3, 200, 209, 320.1, 419, 421, 252.2, 468, 418, 469; 47/58; 800/265, 268, 279, 294, 298, 301

[56] References Cited

U.S. PATENT DOCUMENTS 5,187,262  2/1993  Raikhel et al. ..................... 530/370

FOREIGN PATENT DOCUMENTS 0440304  8/1991  European Pat. Off. .
0460753  12/1991  European Pat. Off. .
9217591  10/1992  WIPO .

OTHER PUBLICATIONS

Hejgaard, J., et al. 'Antifungal activity of chitin-binding . . . ' FEBS Letters, vol. 307, No. 3 (Aug. 1992), Amsterdam NL, pp. 389–392.

Stanford, A., et al. Differential Expression Within a Family Molecular and General Genetics, vol. 215 (1989), Berlin DE, pp. 200–208.

Sela–Buurlage, M.B., et al. 'Only Specific Tobacco . . . ' Plant Physiology., vol. 101, No. 3 (Mar. 1993), Rockville, MD, USA., pp. 857–863.

*Primary Examiner*—David T. Fox
*Attorney, Agent, or Firm*—Ladas & Parry

[57] ABSTRACT

Chimeric genes encoding antifungal chitin binding proteins (antifungal CBPs) with very low chitinase activity (10% or less than that of the class-I chitinases from tobacco). Also substantially pure DNA sequences encoding antifungal CBP are provided for the obtention of transgenic plants producing antifungal CBP. Plants expressing an antifungal CBP gene, optionally in combination with a plant expressible glucanase gene, show reduced susceptibility to fungi.

31 Claims, 5 Drawing Sheets

ANTIFUNGAL CHITIN BINDING PROTEINS AND DNA CODING THEREFOR

This application is a continuation of application(s) Ser. No. 08/411,640 filed on Apr. 5, 1995, now abandoned, which is International Application PCT/EP93/02790 filed on Oct. 5, 1993 and which designated the U.S.

FIELD OF THE INVENTION

The present invention relates to antifungal chitin binding proteins, methods for isolating such proteins and recombinant polynucleotides encoding therefor, as well as plants which have been transformed to contain said recombinant DNA and parts of such plants.

STATE OF THE ART

Proteins that bind to chitin have been identified in various plant species. The family of chitin binding proteins comprises proteins of various nature such as chitinases, occurring inter alia in bean (Boller T. et al, 1983, Planta 157, 22–31), wheat (Molano J. et al., 1979, J. Biol. Chem. 254, 4901–4907), tobacco (Shinsi H. et al., 1987, Proc. Natl. Acad. Sci. USA 84, 89–93), poplar (Parsons, T. J. et al, 1989, P.N.A.S. 86, 7895–7899), and potato (Laflamme D. and Roxby R., 1989, Plant Mol. Biol. 13, 249–250); lectins, occurring inter alia in wheat (WGA) (Rice R. H. & Etzler M. E., 1974 Biochem. Biophys. Res. Commun. 59 414–419), rye (Peumans W. J. et al., 1982, Biochem. J. 203, 239–243), barley (Peumans W. J. et al., supra), rice (Tsuda M., 1979, J. Biochem. 86, 1451–1461), and some other *gramineae* species (see Chrispeels M. J. & Raikhel N. V., 1991, The Plant Cell 3, 1–9, for review).

All chitin binding proteins share a similar amino acid sequence which is called the hevein domain because its approximate 50% homology with a small chitin binding protein found in the latex of the rubber tree *Hevea brasiliensis* (Walujono K. et al., 1975, Proceedings of the International Rubber Conference, Kuala Lumpur, Malaysia, 518–531).

Some chitin binding proteins have been reported to possess antifungal activity in in vitro assays. Bean intracellular chitinase is capable of inhibiting the growth of *Trichoderma viride* at a concentration of at least 2 μg/ml (Schlumbaum A. et al., 1986, Nature 324, 365–367); this chitinase belongs to the so-called class-I chitinases (see: Lawton K. et al., 1992, Plant Mol. Biol. 19, 735–743). Initially, the chitin binding lectins have been reported to possess antifungal activity in in vitro assays (e.a. Mirelman D. et al., 1975, Nature 256, 414–416), but this effect appeared attributable to contaminating chitinases (Schlumbaum et al, 1986, supra). None of the following chitin binding proteins had antifungal activity: tomato and potato lectin (both from Sigma), Pokeweed (*Phytolacca americana*) lectin, gorse agglutinin UEAII, concanavalin A, bean phytohemagglutinin A, peanut agglutinin, osage orange lectin and the wheat germ agglutinin previously tested (Mirelman et al., 1975, supra).

However, of the lectins examined sofar, the small stinging nettle (*Urtica dioica*) agglutinin (UDA) has been shown to possess antifungal activity against chitin-producing fungi (Broekaert W. F. et al., 1989, Science 245, 1100–1102), albeit at very high concentrations; $IC_{50}$=>400 μg/ml. It was established that no chitinase activity was involved in the fungistatic effect of the UDA. This protein has a molecular weight of approximately 8.5 kDa, is particularly rich in cysteine and tryptophane (Peumans W. J. et al., 1983, Fed. Exp. Biol. Soc. Lett. 177, pp99 et seq), has affinity for N-acetyl-D-glucosamine oligomers (Shibuya N. et al., 1986, Arch. Biochem. Biophys. 249, pp215 et seq), and shows a synergistic antifungal effect in combination with chitinase.

The small chitin binding protein of the rubber tree hevein has also been reported to possess antifungal activity against a variety of fungi, including *Trichoderma hamatum* and *Fusarium oxysporum* (Van Parijs et al., Planta 183, 258–264). Its activity was reported to be stronger than tobacco chitinases and somewhat less than that of nettle lectin UDA. Nonetheless, the required concentrations by far exceed physiologically feasible concentrations; the $IC_{50}$ ranges from 90 μg/ml for *Trichoderma hamatum* to 1250 μg/ml for *Fusarium oxysporum*. Its molecular weight as estimated by SDS-PAGE was 14 kDa, but using gel filtration its size was determined at 9–10 kDa.

Several authors speculated about a possible correlation between the small size of both chitin binding proteins and antifungal activity. For instance two small antimicrobial peptides identified more recently, which also fall into the class of antifungal chitin binding proteins, Ac-AMP1 and Ac-AMP2, have a molecular weight of about 3 kDa (Broekaert W. F. et al., 1992, Biochemistry 31, 4308–4314). These authors also noted, that chitin binding proteins which have antimicrobial properties share a number of features, such as a highly basic nature, a small-sized polypeptide chain, and a high content of cysteine.

Another feature that has been reported for the smaller antifungal chitin binding proteins, as well as some other non chitin binding antifungal proteins such as the barley thionins, and the maize protein zeamatin (Roberts W. K. and Selitrennikoff C. P, 1990, J. Gen. Microbiol. 136, 1771–1778), is the loss of antifungal activity in the presence of divalent cations. In view of this ionic-strenth-dependent behaviour, it was therefore considered questionable, whether the Ac-AMPs can exert antifungal effects in their natural microenvironment (Broekaert W. F. et al., 1992, supra). Moreover, given the high concentrations required for antifungal activity in the in vitro assays, it remains to be seen if these proteins are of any use for the engineering of fungal resistant plants.

SUMMARY OF THE INVENTION

The present invention provides a new class of antifungal chitin binding proteins, which are characterized in that they have low chitinase activity, a molecular weight of at least 15 kDa, and a strong synergistic antifungal effect in combination with 1,3-β-glucanases; the antifungal effect of these proteins is not markedly decreased by divalent cations. Preferred antifungal chitin binding proteins are those which have an estimated molecular weight of about 20 kDa using SDS-PAGE and are obtainable from tobacco. Except for the hevein domain, the CBPs according to the invention do not bear much resemblance to the class-I chitinases, as the latter not only have a dissimilar molecular weight, but also lack substantive amino acid homology with the CBPs according to the invention.

The invention also comprises an antifungal composition comprising an antifungal amount of an antifungal CBP according to the invention. Preferred according to the invention is a composition which further comprises glucanase, more preferably an intracellular plant β-1,3-glucanase, yet more preferably from tobacco.

Another aspect of the invention is a substantially pure polynucleotide sequence encoding an antifungal CBP according to the invention. A preferred embodiment is the polynucleotide sequences represented by SEQIDNO: 7 and 9, as well as DNA sequences which hybridize therewith.

Yet another aspect of the invention is a chimeric plant expressible gene encoding an antifungal CBP according to the invention. According to a preferred embodiment of the invention the plant expressible antifungal CBP gene comprises in sequence:

a transcriptional initiation sequence which is functional in a plant cell, and a DNA sequence encoding an antifungal chitin binding protein according to the invention, and optionally, a transcriptional termination sequence that is functional in a plant cell.

The invention also includes plasmids suitable for cloning in a microorganism which plasmid harbours a DNA sequence encoding an antifungal CBP according to the invention. Also included are plasmids harbouring a said DNA sequence and which are suitable for the transformation of plant material. Other embodiments of the invention are microorganims, including Agrobacterium strains, containing a said plasmid or plasmids.

According to another aspect, the invention provides a method for obtaining a plant host which contains a chimeric plant expressible antifungal CBP comprising the steps of:

(1) introducing into a recipient cell of said plant host a chimeric plant expressible antifungal chitin binding protein gene and a selectable marker gene that is functional in said plant host, (2) generating a plant from a recipient cell obtained from step (1) under conditions that allow for selection for the presence of the selectable marker gene.

The invention also provides a recombinant plant DNA genome which contains a chimeric plant expressible gene encoding an antifungal CBP according to the invention. More preferred recombinant plant DNA genomes according to the invention are those which further comprise a chimeric plant expressible 1,3-β-glucanase gene, such that both genes are expressed and the proteins they encode are produced.

The invention further provides plant cells, including protoplasts, which have a recombinant plant DNA genome according to the invention, as well as plants or parts of plants, such as a bulbs, flowers, fruits, leaves, pollen, roots or root cultures, seeds, stalks, tubers (including microtubers) and the like, containing a cell harbouring a recombinant DNA genome according to the invention. More preferred are plants or parts thereof, which substantially consist of cells having a recombinant plant DNA genome according to the invention. Yet more preferred are plants which harbour a recombinant plant DNA genome according to the invention which as a result exhibit reduced susceptibility to fungal infection.

The invention further provides a method for breeding a plant variety which has reduced susceptibility to fungi, characterized in that at least one of the parental lines has a recombinant DNA genome according to the invention. The invention also provides a method for reducing the damage to agricultural crop plants as a result of fungal infection characterized in that a plant is used which exhibits reduced susceptility to fungal infection.

The invention also provides a method for the isolation of an antifungal CBP from plant material comprising the steps of:

(a) preparing an extract from plant material that has been inoculated with a pathogen or elicitor that causes an incompatible reaction in said plant;

(b) separating proteins in the extract according to ionic strength, (c) pooling fractions that contain basic proteins and (d) pooling basic proteins that bind to chitin;

(e) separating the chitin binding proteins obtained after stepd (d) according to molecular weight and (f) testing fractions containing a protein within the molecular weight range of 15 to 25 kDa in an in vitro assay for antifungal activity, (g) isolating a chitin binding protein with antifungal activity.

DETAILED DESCRIPTION OF THE INVENTION

Figure 1:
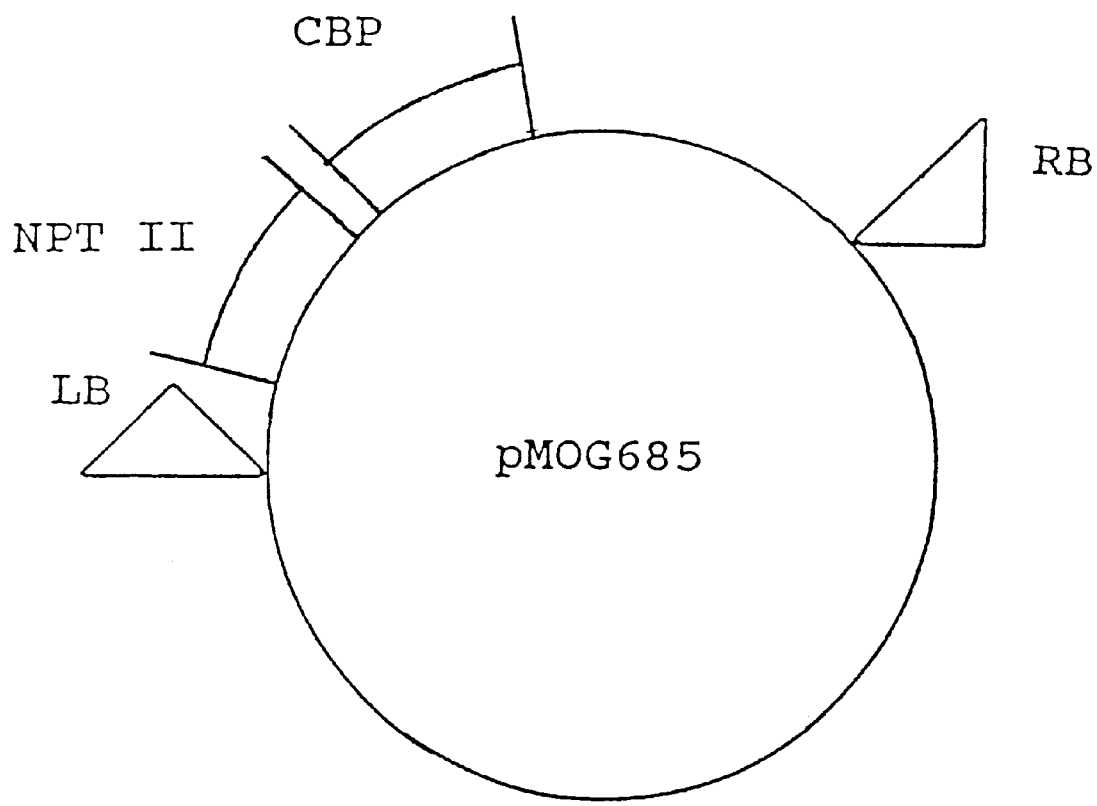
FIG. 1: Binary vector pMOG685, containing in addition to the plant expressible NPTII marker gene a plant expressible fungal chitin binding protein gene.

Two closely related chitin binding proteins with antifungal activity were found in tobacco plants treated with a pathogen or elicitor that cause an incompatible reaction. These proteins clearly do not belong to the known antifungal chitin binding proteins, i.e. class-I intracellular chitinases, or the small chitin binding proteins such as the stinging nettle lectin UDA, the latex protein from *Hevea brasiliensis*, or the small antimicrobial chitin binding proteins from *Amaranthus caudatus*, Ac-AMP1 and Ac-AMP2.

The new CBPs are characterized by a molecular weight in the range of 15 to 25 kDa of the mature protein, a a drastic synergistic antifungal effect in combination with β-1,3-glucanase and low chitinase activity (not more than 10%, more particularly not more than 5% of the class-I chitinases from tobacco as determined with the tritiated chitin method according to Molano et al., 1977, supra). A composition containing 5 μg/ml tobacco CBP and 0.5 μg/ml intracellular β-1,3-glucanase from tobacco almost completely inhibited the growth of *Fusarium solani* and *Trichoderma viride*.

Under the antifungal assay conditions used there were no indications, that the antifungal CBPs according to the present invention are markedly inhibited by divalent cations.

Amino acid sequence determination of the tobacco CBP revealed the presence of a hevein domain similar to other chitin binding proteins. In addition the determined amino acid sequences of the tobacco CBP shows considerable homology with the primary structure of two chitin binding proteins from potato, called win1 and win2 (Stanford A. et al., 1989, Mol. Gen. Genet. 215, 200–208) as deduced from cDNA clones encoding these proteins. The isolation of the proteins themselves was not reported, nor has a physiological role for these two proteins been suggested. On the basis of the amino acid sequence similarity and the presence of a common hevein domain and the almost identical size, we predict that the two chitin binding proteins from potato fall into the category of antifungal chitin binding proteins according to the invention; hence it is expected that these proteins possess as synergistic antifungal activity in combination with β-1,3-glucanases, just as the tobacco antifungal chitin binding proteins.

Moreover, in tomato a 22 kDa protein was detected that shows amino acid sequence similarity with the tobacco CBPs and cross-reacts with antisera that recognise these CBPs. It is therefore concluded, that the tobacco antifungal chitin binding proteins have counterparts in most if not all other plant species, which proteins will have similar size and antigenicity, and which possess antifungal properties similar to the antifungal CBPs of tobacco according to the invention.

Two different DNA sequences encoding tobacco antifungal CBP were isolated from a cDNA library of tobacco leaves inoculated with TMV. A plant chimeric plant expressible gene construct containing a said CBP encoding DNA sequence under the control of the high-level CaMV 35S promoter with double enhancer and the alfalfa mosaic virus (AlMV) untranslated leader was introduced into tobacco and tomato plants and plants producing CBP either intracellularly (unmodified construct) or extracellulary (C-terminal vauolar targeting signal deleted construct) were assayed for fungal resistance using *Rhizoctonia solani* or *Fusarium oxysporum* f. sp. Lycopersici as test fungi. Although plants expressing CBP showed less severe symptoms than non-transgenic control plants, resistance to fungal attack was markedly increased in plants which simultaneously expressed a chimeric plant expressible gene encoding tobacco intracellular β-1,3-glucanase under the control of the same high level regulatory elements as the tobacco antifungal CBP genes. It was shown, that the intracellular tobacco β-1,3-glucanase may as well be targeted to the extracellular space by deletion of the C-terminal vacuolar targeting domain.

To understand the true scope of the invention some aspects will be outlined in somewhat more detail.

Susceptible Fungi

The antifungal effect of tobacco CBP has been demonstrated for *Trichoderma viride, Fusarium solani* in in vitro assays, and *Fusarium oxysporum* and *Rhizoctonia solani* in in planta tests for purposes of illustration. It will be clear, that the use of CBPs according to the invention, or DNA encoding therefore, for use in a process of combating fungi is not limited to the mentioned fungi. There is no reason to assume that the CBPs according to the invention do not possess antifungal activity against a far broader range of fungi than those tested here. Likewise the synergistic effect of CBP and glucanase is likely to apply for a wide range of fungi.

Plant Species

Although the invention is illustrated in detail for transgenic tomato and tobacco plants it should be understood that any plant species that is subject to some form of fungal attack may be provided with one or more plant expressible gene constructs, which when expressed overproduce CBP and/or glucanase in said plant in order to decrease the rate of infectivity and/or the effects of such attack. The invention can even be practiced in plant species that are presently not amenable for transformation, as the amenability of such species is just a matter of time and because transformation as such is of no relevance for the principles underlying the invention. Hence, plants for the purpose of this description shall include angiosperms as well as gymnosperms, monocotyledonous as well as dicotyledonous plants, be they for feed, food or industrial processing purposes; included are plants used for any agricultural or horticultural purpose including forestry and flower culture, as well as home gardening or indoor gardening, or other decorative purposes.

Transformation

In principle any transformation method may be used to introduce a plant expressible gene according to the invention into a plant species of choice. Generally, useful methods are the calcium/polyethylene glycol method for protoplasts (Krens, F. A. et al., 1982, Nature 296, 72–74; Negrutiu I. et al, June 1987, Plant Mol. Biol. 8, 363–373), electroporation of protoplasts (Shillito R. D. et al., 1985 Bio/Technol. 3, 1099–1102), microinjection into plant material (crossway A. et al., 1986, Mol. Gen. Genet. 202, 179–185), (DNA or RNA-coated) particle bombardment of various plant material (Klein T. M. et al., 1987, Nature 327, 70), infection with viruses and the like.

In a preferred embodiment of the invention use is made of Agrobacterium-mediated DNA transfer. Especially preferred is the use of the so-called binary vector technology as disclosed in EP-A 120 516 and U.S. Pat. No. 4,940,838).

Generally, after transformation plant cells or cell groupings are selected for the presence of one or more markers which are encoded by plant expressible genes co-transferred with the plant expressible gene according to the invention, whereafter the transformed material is regenerated into a whole plant.

Although considered somewhat more recalcitrant towards genetic transformation, monocotyledonous plants are amenable to transformation and fertile transgenic plants can be regenerated from transformed cells or cell groupings. Presently, preferred methods for transformation of monocots are microprojectile bombardment of explants or suspension cells, and direct DNA uptake or electroporation (Shimamoto, et al, 1989, Nature 338, 274–276). Transgenic maize plants have been obtained by introducing the *Streptomyces hyaroscopicus* bar-gene, which encodes phosphinothricin acetyltransferase (an enzyme which inactivates the herbicide phosphinothricin), into embryogenic cells of a maize suspension culture by microprojectile bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selecting only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots.

Monocotyledonous plants, including commercially important crops such as corn are also amenable to DNA transfer by Agrobacterium strains (Gould J, Michael D, Hasegawa O, Ulian E C, Peterson G, Smith R H, (1991) Plant. Physiol. 95, 426–434).

Gene Expression

In order to be expressed in a plant cell a DNA sequence is generally linked to a regulatory sequence, which should at least comprise a trancriptional initiation site; such a promoter is occasionally referred to in the art as a 'minimal promoter'. Regulatory sequences may include additional elements such as enhancers to promote transcription. Enhancers may increase expression in a constitutive fashion or in a tissue-specific or developmentally, or environmentally regulated fashion. Preferred according to the invention are constitutive high-level promoters, such as the CaMV 19S promoter and the CaMV 35S promoter, or the promoters derivable from the T-DNA of Ti-plasmids from Agrobacterium. This promoter may be flanked by so-called enhancer sequences to further enhance expression levels. From the literature it is known that the duplication of the sequence between −343 and −90 of the CaMV 35S promoter increases the activity of the CaMV 35S promoter (Kay R. et al. (1987), Science 236, 1299–1302). Other examples of high-level promoters are the light-inducible ribulose bisphosphate carboxylase small subunit (rbcSSU) promoter and the chlorophyl a/b binding protein (Cab) promoter. It may be desirable to restrict expression of the introduced chimeric genes to one or a few pre-selected tissues, for instance those that are targets for fungal attack, such as roots and epidermal cells, and the like. A well known example of a tissue-specific promoter is for example the patatin class-II promoter.

The invention also embraces the use of hybrid promoters, i.e. promoters that comprise elements derived from regulatory elements of different genes.

Plant expressible genes generally comprise a so-called terminator sequence including a polyadenylation signal. Suitable terminators may be selected from homologous or heterologous genes, the choice is not critical to the invention.

The word 'gene' as used here is meant to comprise cDNAs as well as transcribed regions of genomic clones, either of which may be synthetic or partially synthetic. 'Plant expressible gene' shall mean a DNA sequence which is operably linked to a regulatory sequence required for transcription in a plant cell and which yields RNA upon transcription which can be translated into protein. A gene is 'plant expressible' if it is expressed at least in one tissue in one particular phase of the life cycle of the plant. A gene is understood to be plant expressible even if it is not expressed 'of its own motion' but must be triggered or induced by an external stimulus, such as pathogen attack.

A chimeric plant expressible gene according to the invention is a plant expressible gene which at least combines two sequences that are not naturally associated. For instance chimeric plant expressible genes may comprise genes which comrise combinations of functional regions of a eukaryotic gene such as enhancers, transcription initiation regions, coding regions, non-translated leaders, signal sequences, vacuolar targeting sequences, terminator sequences, introns, exons, and the like, or parts thereof. Preferred according to the invention are chimeric plant expressible genes which comprise a gene encoding an antifungal CBP according to the invention linked to a promoter not naturally associated therewith.

Targeting

A very effective site of action of hydrolytic enzymes in the protection of transformed plants against a range of plant pathogenic fungi is believed to be the apoplastic space. Hence, to obtain improved fungal resistance it is advantageous if plants are transformed with a recombinant DNA construct comprising a gene encoding a plant expressible gene according to the invention which exerts its action in the apoplastic space of the plant, either naturally or by virtue of genetic modification.

Naturally intracellular genes may be modified such that the C-terminal amino acids involved in vacuolar targeting are not present (e.g. by introducing a translational stopcodon in the coding region of the gene, or otherwise), resulting in apoplast-targeting of the vacuolar protein produced in that plant.

Evaluation of Transgenic Plants

Subsequently transformed plants are evaluated for the presence of the desired properties and/or the extent to which the desired properties are expressed. A first evaluation may include the level of expression of the newly introduced genes, the level of fungal resistance of the transformed plants, stable heritability of the desired properties, field trials and the like.

Secondly, if desirable, the transformed plants can be cross-bred with other varieties, for instance varieties of higher commercial value or varieties in which other desired characteristics have already been introduced, or used for the creation of hybrid seeds, or be subject to another round of transformation and the like.

Synergy

The combination of the tobacco antifungal chitin binding protein according to the instant invention and the tobacco β-1,3-glucanase showed a drastic synergistic antifungal effect.

Similar synergistic antifungal effects are expected if combinations of antifungal CBPs according to the invention are combined with β-1,3-glucanases from other plant origins.

In European Pat. No. Application 440 304 A1 it was disclosed that simultaneous overexpression of a plant expressible glucanase gene in conjunction with an intracellular class-I chitinase from tobacco in transgenic plants results in a higher level of resistance to fungi than in plants expressing a plant expressible class-I chitinase alone. Since expression of glucanase alone does not yield resistant plants, it may be concluded that there is a synergistic effect of glucanase and intracellular class-I chitinases.

Both chitinases, glucanases and the new antifungal chitin binding proteins accumulate in infected plant tissues upon an incompatible pathogen-plant interaction. Apparently, the synergizing effect of combinations of pathogen induced proteins is a more general phenomenon that has important consequences for the engineering of fungal resistant plants.

From these observations we predict, that the antifungal CBPs according to the invention will show a synergistic effect with many other proteins that bind to chitin or degrade chitin such as chitinases. Examples of synergizing proteins that may be used in combination with antifungal CBPs according to the invention include, but are not limited to, β-1,3-glucanases and chitinases which are obtainable from barley (Swegle M. et al., 1989, Plant Mol. Biol. 12, 403–412; Balance G. M. et al., 1976, Can. J. Plant Sci. 56, 459–466 Hoj P. B. et al., 1988, FEBS Lett. 230, 67–71; Hoj P. B. et al., 1989, Plant Mol. Biol. 13, 31–42 1989), bean (Boller T. et al, 1983, Planta 157, 22–31; Broglie K. E. et al. 1986, Proc. Natl. Acad. Sci. USA 83, 6820–6824; Vdgeli U. et al., 1988 Planta 174, 364–372); Mauch F. & Staehelin L. A., 1989, Plant-Cell 1, 447–457); cucumber (Metraux J. P. & Boller T. (1986), Physiol. Mol. Plant Pathol. 28, 161–169); leek (Spanu P. et al., 1989, Planta 177, 447–455); maize (Nasser W. et al., 1988, Plant Mol. Biol. 11, 529–538), oat (Fink W. et al., 1988, Plant Physiol. 88, 270–275), pea (Mauch F. et al. 1984, Plant Physiol. 76, 607–611; Mauch F. et al., 1988, Plant Physiol. 87, 325–333), poplar (Parsons, T. J. et al, 1989, P.N.A.S. 86, 7895–7899), potato (Gaynor J. J. 1988, Nucl. Acids Res. 16, 5210; Kombrink E. et al. 1988, Proc. Natl. Acad. Sci. USA 85, 782–786; Laflamme D. and Roxby R., 1989, Plant Mol. Biol. 13, 249–250), tobacco (e.g. Legrand M. et al. 1987, Proc. Natl. Acad. Sci. USA 84, 6750–6754; Shinshi H. et al. 1987, Proc. Natl. Acad. Sci. USA 84, 89–93), tomato (Joosten M. H. A. & De Wit P. J. G. M. 1989, Plant Physiol. 89, 945–951), wheat (Molano J. et al., 1979, J. Biol. Chem. 254, 4901–4907), and the like.

The cloning of plant genes corresponding to proteins that can suitably be used in combination with genes encoding antifungal CBPs according to the invention and the overexpression of such genes in transgenic plants, as well as the assessment of antifungal activity in planta is very well within the scope of the skilled artisan, as is exemplified inter alia in Application WO90/07001 A1, EP-A 392 225, EP-A 440 304 A1, EP-A 460 753 A2, and the like.

Multiple Transgenic Plants

To obtain transgenic plants capable of constitutively expressing more than one chimeric gene, a number of alternatives are available, which are encompassed by the present invention, including the following:

A. the use of one recombinant polynucleotide, e.g a plasmid, with a number of modified genes physically coupled to one selection marker gene.

B. Cross-pollination of transgenic plants which are already capable of expressing one or more chimeric genes coupled to a gene encoding a selection marker, with pollen from a transgenic plant which contains one or more gene constructions coupled to another selection marker. Afterwards the seed, which is obtained by this crossing, is selected on the basis of the presence of the two markers. The plants obtained from the selected seeds can afterwards be used for further crossing.

C. The use of a number of various recombinant polynucleotides, e.g. plasmids, each having one or more chimeric genes and one other selection marker. If the frequency of cotransformation is high, then selection on the basis of only one marker is sufficient. In other cases, the selection on the basis of more than one marker is preferred.

D. Consecutive transformations of transgenic plants with new, additional chimeric genes and selection marker genes.

E. Combinations of the above mentioned strategies. The actual strategy is not critical with respect to the described invention and can be easily determined depending on factors such as the desired construct, the materials available and the preference of the skilled workers.

Advantages

Plants, or parts thereof of commercial interest, with improved resistance against phytopathogenic fungi can be grown in the field or in greenhouses, and subsequently be used for animal feed, direct consumption by humans, for prolonged storage, used in food- or other industrial processing, and the like. The advantages of the plants, or parts thereof, according to the invention are the decreased need for fungicide treatment, thus lowering costs of material, labour, and environmental pollution, or prolonged shelf-life of products (e.g. fruit, seed, and the like) of such plants.

EXPERIMENTAL

Obtention of Agrobacterium strain MOG101

A helper plasmid conferring the *Agrobacterium tumefaciens* virulence functions derived from the octopine Ti-plasmid pTiB6 was constructed, MOG101. MOG101 is a *Agrobacterium tumefaciens* strain carrying a non-oncogenic Ti-plasmid from which the entire T-region was substituted by a bacterial Spectinomycin resistance marker from transposon Tn 1831 (Hooykaas et al., 1980 Plasmid 4, 64–75).

Figure 2:
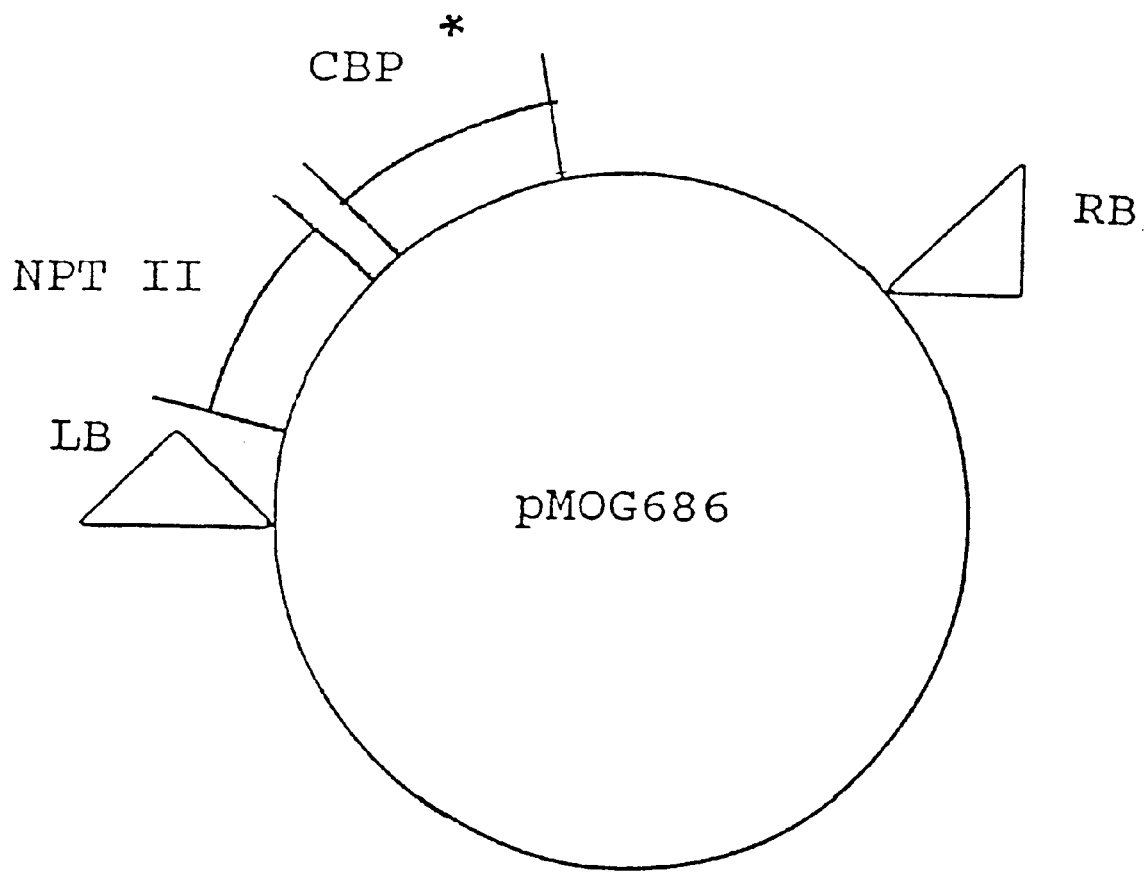
FIG. 2: Binary vector pMOG686, containing in addition to the plant expressible NPTII marker gene a plant expressible, C-terminally modified (*), chitin binding protein gene; the modified CBP is targeted to the extracellular space.
Figure 3:
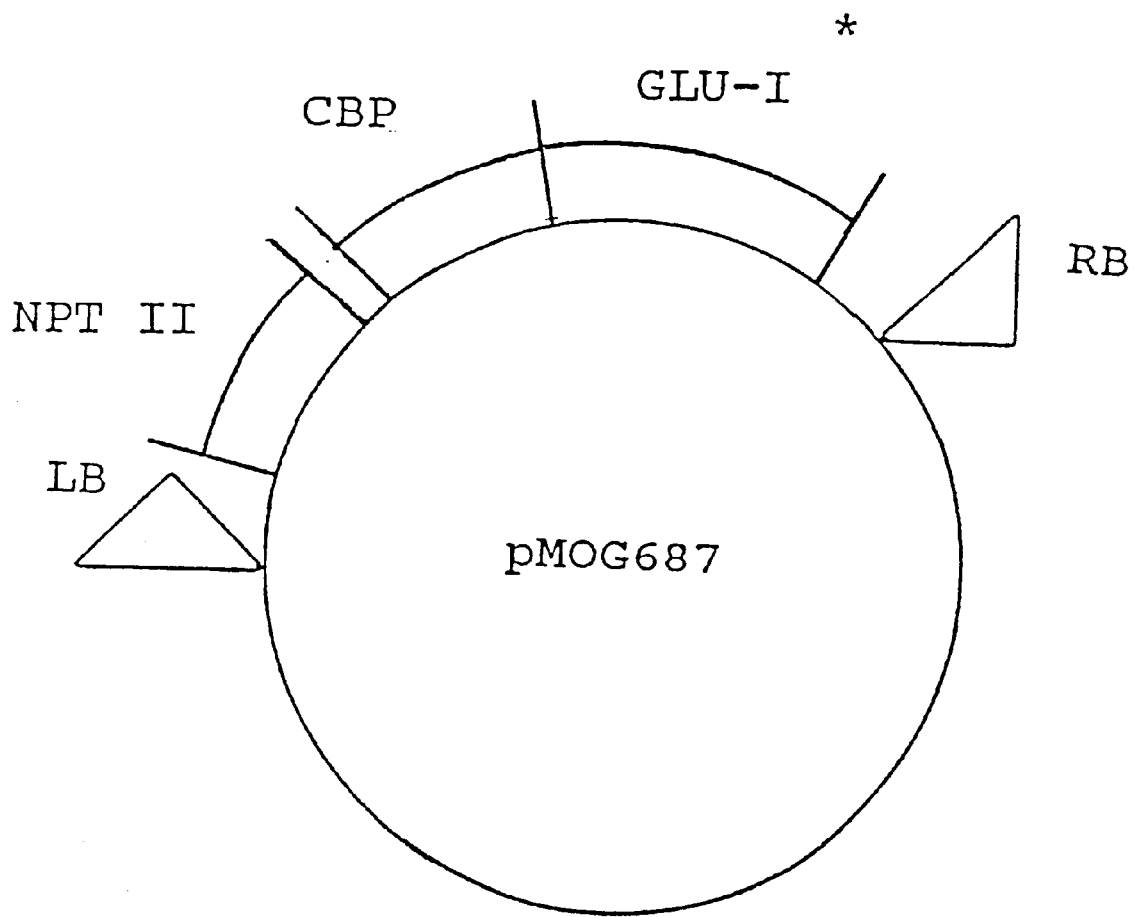
FIG. 3: Binary vector pMOG687 containing in addition to the plant expressible NPTII marker gene an unmodified plant expressible CBP gene and a C-terminally modified (*) plant expressible glucanase gene; the glucanase encoded by this gene is targeted to the extracellular space.
Figure 4:
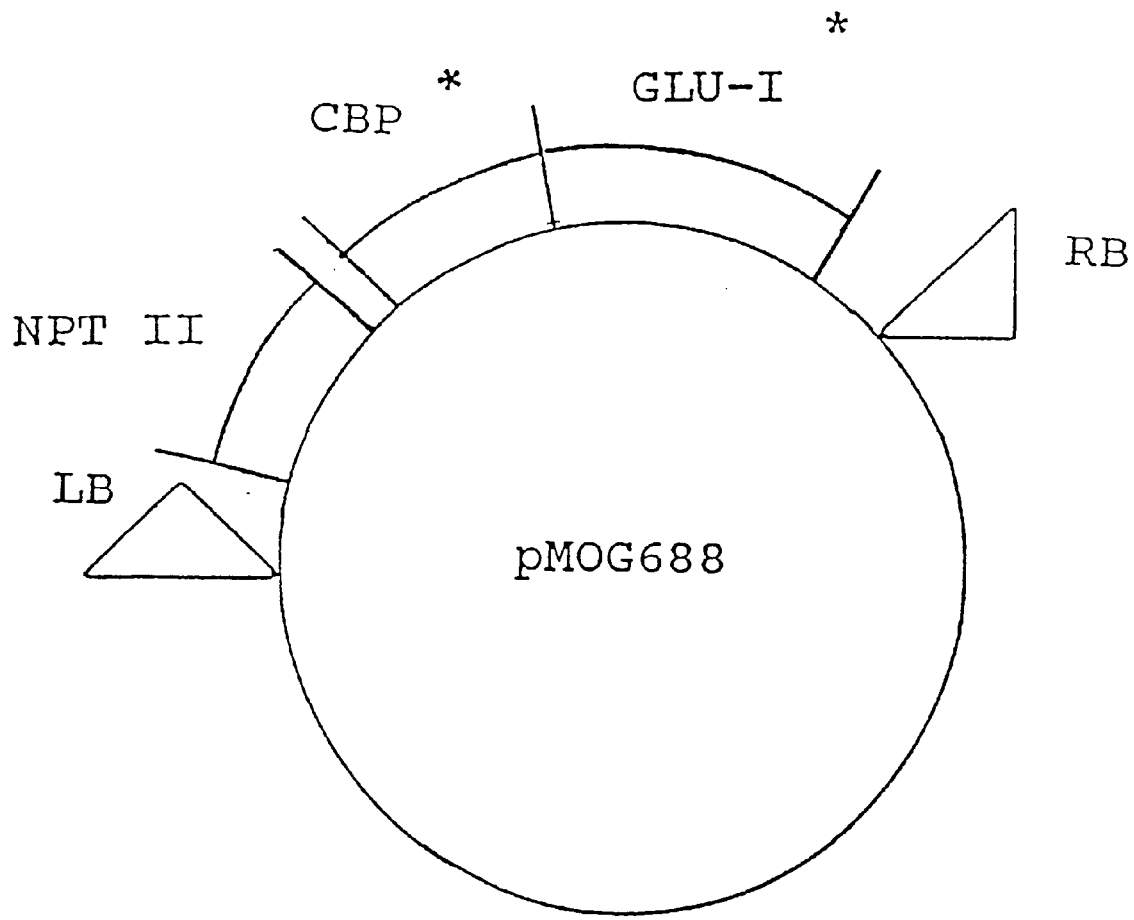
FIG. 4: Binary vector pMOG688 containing in addition to the plant expressible NPTII marker gene a plant expressible, C-terminally modified (*), CBP gene and a plant expressible, C-terminally modified (*), glucanase gene; both the glucanase and the CBP encoded by these genes are targeted to the extracellular space.
Figure 5:
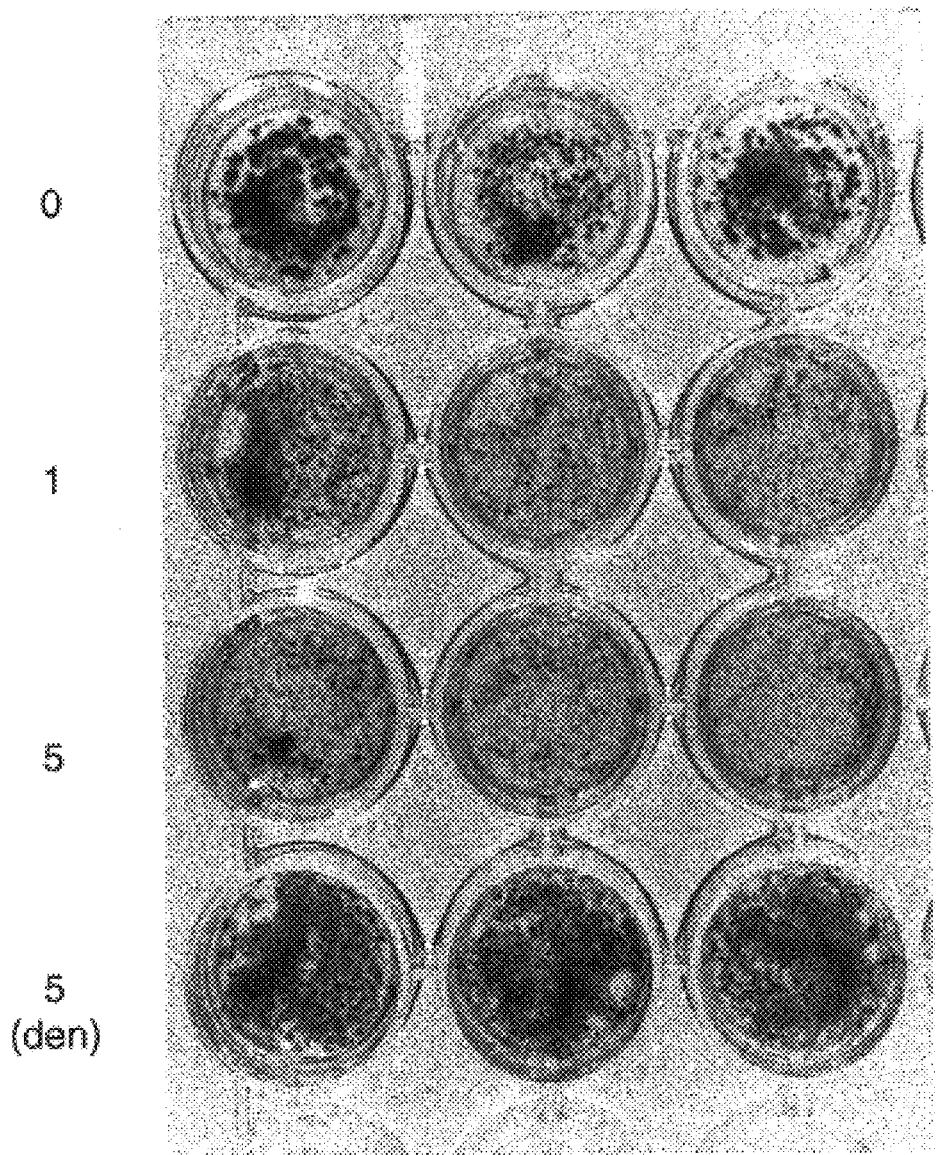
FIG. 5: Effect on growth of *Fusarium solani* of CBP, and combination of CBP with either intracellular glucanase (Glu-I) or class-I chitinases in a microtiter plate assay. den=denatured protein mixtures.

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG621 is a pBR322 derivative, which contains the 2 Ti-plasmid fragments that are located to the left and right, outside the T-regions (FIG. 2). In pMOG579 the 2 fragments (shown in dark) were separated by a 2.5 kb BamHI-HindIII fragment from transposon Tn1831 (Hooykaas et al., 1980 Plasmid 4, 64–75) carrying the spectinomycin resistance marker (FIG. 2). The plasmid was introduced into *Agrobacterium tumefaciens* strain LBA1010 [C58-C9 (pTiB6)=a cured C58 strain in which pTiB6 was introduced (Koekman et al. (1982), Plasmid 7, 119–132) by triparental mating from *E.coli*, using HB101 8pRK2013) as a helper. Transconjugants were selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants replica plated onto carbenicillin (100 mg/l) 2 were found sensitive. Southern analysis showed that a double crossing over event had deleted the entire T-region (not shown). The resulting strain was called MOG101. This strain and its construction is analogous to strain GV2260 (Deblaere et al. 1985, Nucl. Acid Res. 13, 4777–4788).

EXAMPLE 1

Leaves of 7 to 8 weeks old Samsun NN tobacco plants were inoculated with tobacco mosaic virus (TMV). Seven days after inoculation 400 grams leaves were harvested and homogenized at 4° C. in 500 ml 0.5 M NaOAc pH5.2, 15 mM 2-mercapto-ethanol, and 4 gram active carbon, using a Waring blendor. The homogenate was filtered over four layers of cheese cloth and subsequently the filtrate was centrifuged for 15 minutes at 3,000 g. The supernatant was centrifugated for 50 minutes at 20,000 g and desalted by passage through a Sephadex G25 column (medium course; Pharmacia), length 60 cm, diameter 11.5 cm, and equilibrated in 4 OmM NaOAc pH 5.2. The desalted protein solution was stored overnight at 4° C. and subsequently centrifugated during 45 minutes at 20,000 g. The supernatant was passed through a S-sepharose (Fast Flow, Pharmacia) column, length 5 cm, diameter 5 cm, which was equilibrated with 40 mM NaOAc pH 5.2. The column was washed with the above mentioned buffer (flow rate 400 to 500 ml/hr) until the $OD_{280}$ dropped to zero. The unbound proteins were collected. The bound proteins were eluted using an increasing linear NaCl gradient (o to 300 mM) in 500 ml of the above mentioned buffer, and a flow rate of 3 ml per minute; fractions of approximately 5 ml were collected. All fractions were assayed for chitinase activity.

Chitinase activity was assayed radiometrically with tritiated chitin as substrate (Molano et al 1977, Anal. Biochem. 83, 648–656). The specific activity of the final product was approximately $1.2 \times 10^6$ cpm/mg. Before use the tritiated chitin was washed three times. To 100 μl 10 mM potassium phosphate buffer pH 6.4 with 0.02% sodium azide, 50 μl tritiated chitin (approximately 150,000 counts per minute, cpm) and 50 μl protein solution was added. The mixture was incubated while shaking for 30 minutes at 37° C. The reaction was stopped by adding 600 μl 10% trichloro acetic acid. After centrifugation to pellet the chitin (10 minutes in a microfuge), 500 μl supernatant was filtered over glasswool and pipetted into a scintillation vial. 5 ml scintillation fluid was added and the radioactivity released (expressed as counts per minute) was taken as a measure for chitinase activity.

The fractions containing chitinase activity were pooled and concentrated by ultrafiltration through an Amicon membrane (cut off 10 kDa). The concentrated fraction was brought to 20 mM $NaHCO_3$ and the pH was adjusted to 8.3 with NaOH. Subsequently, the fraction was adsorbed to 50 ml regenerated chitin (Molano et al., 1977) equilibrated in 20 mM $NaHCO_3$. The chitin matrix was washed with 100 ml 20 mM $NaHCO_3$ and subsequently with 100 ml 20 mM NaOAc pH 5.2. Bound proteins were eluted with approximately 150 ml 20 mM HAc (pH 3.5). The protein containing fractions were dialyzed against 0.2 M NaCl, 50 mM $K_2HPO_4/KH_2PO_4$, pH 7.0 and subjected to gelfiltration chromatography on a Superdex 75 column (HR 10/30; Pharmacia) at a flow rate of 0.5 ml per minute. Fractions of approximately 0.5 ml were collected. Each fraction was analyzed by electrophoresis (Laemmli, Nature 227, 680–685) using a 12.5% polyacrylamide gel in the presence of sodium dodecyl sulphate (SDS), using molecular weight markers of (18–97 kD) as reference. A separate portion of each fraction was tested for chitinase activity. Fractions containing a 32 kD proteins could be identified as the two isoforms of class I tobacco intracellular chitinase (Shinshi et al., 1990). Fractions containing solely (as judged by electrophoresis) a 20 kD protein with an approximate retention time of 30 minutes, were found to contain very low chitinase activity (specific activity 50–100 times lower than class I chitinases). These fractions were pooled and the 20 kD protein in the pooled fraction was called Chitin Binding protein (CBP).

The antifungal activity of CBP was assessed in a microtiter plate assay using the fungi *Trichoderma viride* and *Fusarium solani*. In each well of a 24-well microtiter dish 250 μl potato dextrose agar (PDA) was pipetted. Fungal spores were suspended in water and 400–600 spores in 50 μl were added to the wells. Spores were pregerminated 6 to 16 hours at 25° C. Subsequently 100 μl filter sterilized (0.22 gm filter) protein solution (in 50 mM $K_2HPO_4/KH_2PO_4$,pH 6.0) was added. Microtiter dishes were wrapped with Parafilm and incubated at room temperature. At several timepoints after the initiation of incubation the fungus was monitored microscopically for effects of the added protein. After 2–3 days the mycelium of the growing fungus in the wells was stained with lactophenol cotton blue and the extent of growth was estimated. With *T. viride* addition of 1 μg purified CBP per well resulted in lysis of the hyphal tips of the fungus. Moreover, an inhibition of growth could be observed. One to ten μg of CBP was not sufficient to lyse hyphal tips of *F. solani* or to inhibit the growth of the fungus. However, microscopically a clear swelling of tips was observed.

An amount of 0.5 μg purified tobacco intracellular β-1, 3-glucanase (in 50 mM $K_2HPO_4/KH_2PO_4$,pH 6.0) per well did not show any effect on either *T. viride* or *F. solani* in the antifungal assay. The addition of a protein solution containing 5 μg CBP and 0.5 μg β-1,3-glucanase showed a very drastic inhibition of growth of *F. solani*. Apparently CBP and β-1,3-glucanase show a synergistic effect in the inhibition of the growth of fungi.

The synergistic antifungal effect of CBP with class-I intracellular chitinases was tested on *Fusarium solani* and *Alternaria radicina*. The results are summarised in the table 1 and 2.

TABLE 1

Antifungal effect of CBP and synergistic antifungal effect of CBP with intracellular β-1,3-glucanase or intracellular class-I chitinase on *Fusarium solani*

| CBP | | glu-I — | 0.5 μgr | — |
|---|---|---|---|---|
| | chi-I | — | — | 0.5 μgr |
| 0 | | GI = 0 | <5%, GI = 1 | <5%, GI = 0 |
| 1 μgr | | GI = 1 | 70%, GI = 3 | <5%, GI = 3 |
| 5 μgr | | GI = 3 | 70%, GI = 3 | <5%, GI = 3 |
| 5 μgr (den) | | GI = 0 | <5%, GI = 0 | <5%, GI = 0 |

Lysis is indicated by a percentage with respect to untreated control. GI: growth inhibition; a scale of 0–4 is used, 0 = no visible inhibition, 1 = weak inhibition, 2 = moderate inhibition, 3 = strong inhibition, 4 = very strong inhibition. (den) = denatured protein mixtures.

CBP does not cause lysis of *Fusarium solani*, but it has a strong growth inhibitory effect at 5 μg. Chitinase as such has no lytic effect on *Fusarium solani* at 0.5 μg, but in combination with 1 μg CBP it has a strong growth inhibitory effect.

The combination of 1 μg CBP and 0.5 μg glucanase causes lysis (70%) as well as a strong growth inhibiting effect on *Fusarium solani*. It is concluded that CBP has a synergistic antifungal effect in combination with glucanases as well as with class-I chitinases.

TABLE 2

Growth inhibitory effect of CBP and intracellular β-1,3-glucanase or class-I chitinase on *Alternaria radicina*

| CBP | — | 0.1 μg glu-I | 0.5 μg chi-I |
|---|---|---|---|
| 0 | 0 | 0 | 1–2 |
| 1 μg | 0 | 0–1 | 1–2 |
| 5 μg | 0–1 | 1 | 2 |
| 5 μg (den) | 0 | 0 | 0 |

The scale and abbreviations are as in Table 1.

The results in table 2 indicate a synergistic antifungal effect of CBP and intracellular glucanase and at least an additive effect of CBP and class-I chitinase on *Alternaria radicina*. At 5 μg per well, CBP has a growth inhibitory effect on *Alternaria radicina*, albeit rather weak.

Further in vitro antifungal activities have been determined with *Alternaria porri* as test fungus. Up to 10 μg CBP had no detectable effect against *A. porri*, whereas 5 μg CBP in combination with 0.3 μg intracellular β-1,3-glucanase from tobacco has a moderate growth inhibitory effect on *a. Porri* (GI=2 on the above scale). β-1,3-glucanase alone had no effect at 0.3 μg, whereas 2.5 μg had a moderate (GI=2) growth inhibitory effect on *A. porri*. The combined data again indicate a synergistic effect between CBP and β1,3-glucanase.

To characterize CBP further its amino acid sequence was partially determined. Initial experiments to elucidate the amino (N)-terminal sequence of CBP directly were not successful suggesting that the N-terminus is blocked. To obtain internal sequences, about 20 μg CBP was digested with endoproteinase Glu-C ($V_8$ protease) according to Cleveland et al. (1977, J. Biol. Chem. 252 1102–1106). $V_8$ protease cuts proteins at glutamic acid residues. The digestion products were run over a 12.5% polyacrylamide gel containing 0.05% SDS (Laemmli, supra) and electroblotted onto a PVDF membrane as described by Matsudaira et al. (1987, J. Biol. Chem. 262, 10035–10038). The protein band migrating as a polypeptide 3–4 kDa smaller than the undigested material, was cut out of the gel and sequenced using Edman degradation on an Applied Biosystems 477A protein sequencer according to the protocol provided by the manufacturer. The following sequence was obtained:
(E) Y (A/G) S P S Q G ? Q S Q (R) S G G G G (G/R) G G G G G G G A Q N (SEQIDNO: 2). The amino acid sequence is given using the one-letter code. Amino acid 1 (E) was not determined, but since $V_8$ protease cuts proteins at glutamic acid residues, it has been placed at that position. Amino acids 3 (A/G), 13 (G/R) and 19 (R) could not be determined unambiguously and amino acid 9 (?) is most likely a cysteine residue.

To obtain additional sequences 20 μg CBP was run over a 12.5% polyacrylamide gel containing 0.05% SDS (Laemmli, suira). The protein was visualized and cleaved in situ with Nedlorosuccinimide/urea (NCS) according to Lischwe and Ochs (1982, Anal. Biochem. 127. 453–457). NCS cleaves proteins at tryptophan residues. The digestion products were separated on a 17.5% polyacrylamide gel containing SDS and electroblotted onto a PVDF membrane according to Matsudaira et al. (1987, J. Biol. Chem. 262, 10035–10038). The polypeptide migrating on the gel as a 9–11 kDa protein was cut out and sequenced using Edman degradation on an Applied Biosystems 477A protein sequencer according to the protocol provided by the manufacturer. The following sequence was obtained:
(W) T A F (Y) G P V G P (P/R) G R D S (SEQIDNO: 1). The amino acid sequence is given using the one-letter code. Amino acid 1 (W) was not determined, but since NCS cuts proteins at tryptophan residues, it has been placed at that position. Amino acids 5 (Y) and 11 (P/R) could not be determined unambiguously.

Comparison of the two elucidated sequences with known sequences in a data bank, revealed a high degree of homology of both sequence 1 and 2 with the amino acid sequences deduced from two potato genes whose expression is induced by wounding and which are known as the win 1 and win 2 genes (Stanford et al. 1988, Mol. Gen. Genet. 215, 200–208). As far as known the win proteins themselves have never been identified and isolated. Neither has it been established that these proteins possess an antifungal activity. However, on the basis of our results we predict that win-proteins and other CBP-like proteins in the plant kingdom will possess a similar antifungal property as CBP.

Except for win 1 and win 2 sequences, the primary structure of the tobacco extracellular proteins PR-4a and PR-4b (Linthorst et al. 1991, Mol. Plant-Microbe Interact. 4. 586–592) and the tomato extracellular protein P2 (Linthorst et al., supra) show homology with sequence 1 as well. The tobacco PR-4 proteins and the tomato P2 protein are serologically related (Joosten et al., 1990, Plant Physiol. 94, 585–591). Antisera raised against either the PR-4 proteins or P2 cross-react with CBP. However, in contrast to CBP the tobacco PR-4 proteins do not exert a fungal growth inhibiting activity.

From extracts of leaves of *Cladosporium fulvum* infected Moneymaker tomato plants we have been able to isolate a chitin binding protein of approximately 20 kD which is serologically related to both the tobacco PR-4 proteins and the tomato P2 protein.

EXAMPLE 2

Cloning of cDNA's Corresponding with CBP and Preparation of the Binary Vector pMOG685

A tobacco cDNA library was made using a ZAP-cDNA synthesis kit (Stratagene Cat #200400, 200401). From TMV-infected Samsun NN tobacco leaves, polyadenylated RNA was isolated and used for the synthesis of CDNA as described by Linthorst et al. (1990, Mol. Plant-Microbe Interact., 3: 252–258). After treatment with EcoRI and XhoI, the cDNA fragments were ligated to the compatible termini of the lambda ZAP arms.

The attempts to isolate CBP clones from the lambda ZAP-cDNA library using a PR4 cDNA probe were not successful. Therefore, the above described lambda ZAP tobacco cDNA library was screened with a specific DNA probe for sequences that are coding for CBP. A specific CBP CDNA fragment (407 bp) was obtained from a total lambda ZAP-cDNA library by PCR amplification using the oligonucleotides SEQIDNO: 3 and SEQIDNO: 4 as primers. SEQIDNO: 3 is complementary to the pSK-vector sequence of the lambda ZAP arm at the 5'-end of the cDNA gene. SEQIDNO: 4 is deduced from the partial amino acid sequence (SEQIDNO: 1) as determined from CBP (see EXAMPLE 1). The CBP cDNA-fragment was cloned as a EcoRI fragment into the EcoRI linearized vector pBluescript (pBS) plasmid to yield clone pMOG684. The nucleotide sequence of the EcoRI-fragment of clone pMOG684 was determined using the double strand DNA sequencing method,(Chen J. & Seeburg P. H., 1985, DNA 4, 165–170) and showed that a partial CBP cDNA clone was isolated. With the use of PCR and oligonucleotides SEQIDNO: 5 and SEQIDNO: 6, a 187 bp fragment was amplified from the CBP clone pMOG684 and used as a specific probe for isolating additional CBP cDNAs. With the aid of the plaque hybridisation technique from Benton and Davis (1977, Science 196, 180–182) approximately 55 recombinant phages were identified. PCR analysis of purified phage DNA indicated five candidates which contained large cDNA inserts. The inserts in the DNA of these phages were subcloned in a pBluescript (SK⁻) plasmid, using the in vivo excision method. The nucleotide sequence of the different cDNA clones was determined using the double strand DNA sequencing method (Chen E. J. and Seeburg, 1985, DNA 4, 165–170). These analyses in combination with the comparisons of the partial amino-acid sequence of the CBP showed that two types of cDNA clones had been isolated. Clone CBP44 (SEQIDNO: 7) represents a cDNA coding for the said CBP (SEQIDNO: 8; note that this sequence is lacking the intial methionin). Clone CBP52 (SEQIDNO: 9) encodes a CBP (SEQIDNO: 10) having 97% identity with the initially isolated protein. With the use of PCR a BamHI recognition site and an Adenine-Thymidine dinucleotide is introduced in front of the CBP cDNA clone CBP44, hence creating a translation initiation codon; behind the gene a BamHI recognition site was introduced. For these PCR reactions the oligonucleotides SEQIDNOs: 11 and 12 were used as primers. The modified cDNA sequence was verified for undesirable mutations that can occur as a consequence of the PCR method. The sequence with its BamHI linkers is shown in the sequence protocol as SEQIDNO: 13; note that the introduced stop codon is not included in SEQIDNO: 13. The CBP gene was cloned as a BamHI fragment into the BamHI linearized vector pMOG180 (described in EP-A 460 753 A1). The expression construct obtained contains on a EcoRI-HindIII fragment the cauliflower mosaic virus (CaMV) 35S promoter in front of the CBP gene which in its turn is followed by the nopaline synthase (nos) transcription terminator. The expression construct was cloned into the EcoRI-site of the binary vector pMOG23 (deposited at the Centraal Bureau voor Schimmelcultures, Baarn, The Netherlands, No. CBS 102.90) with the aid of the synthetic double-stranded, partially complementary, adapter sequences: 5'-AGCTCACG-3' and 3'-GTGCTTAA-5'. The plasmid thus obtained, pMOG685 (FIG. 1), now contains both the CBP gene, as well as the NPTII gene localized between the left and right T-DNA border sequences. A derivative of this binary plasmid was constructed by insertion of a SstI fragment containing the CaMV 35S promoter in front of a modified tobacco basic β-1,3-glucanase gene encoding an extracellular targeted protein (for details of construction, see EP-A 440 304 A1), into the SstI-site of plasmid pMOG685. The resulting plasmid pMOG687 contains the following expression constructs, the CBP gene, the modified basic β-1,3-glucanase gene and the NPTII gene localized between the left and right T-DNA border sequences. With the aid of plasmid pRK2013, these binary vectors were mobilized indepentdently from E.coli DH5α to Agrobacterium tumefaciens strain MOG101. The transconjugants MOG101(pMOG685) and MOG101(pMOG687) were isolated from these matings on selection medium containing 40 mg/l rifampicin, 250 mg/l spectinomycin, and 100 mg/l kanamycin.

EXAMPLE 3

Construction of pMOG686 Encoding an Extracelullarly Targeted CBP

Wild-type CBP is found intracellularly, most likely in vacuoles of plant cells. To provide for secretion of CBP into the extracellular space, a translational stop-codon is introduced into wild-type CBP cDNA as present in pMOG685, between codon 13 and 14 as numbered from the C-terminal end of the protein encoded by the cDNA. Using PCR technique a stop-codon is created by the insertion of a Thymidine (T) residue between nucleotide 619 and 620 with respect to the sequence presented in SEQIDNO: 13 in the sequence protocol. This modified CBP sequence was checked for undesired mutations that might occur as a consequence of the PCR methodology. The mutated cDNA encodes a CBP lacking the 13 C-terminal amino acids of the primary translation product of the wild-type CBP mRNA. The binary vector thus obtained was called pMOG686 (modified CBP) and the corresponding Agrobacterium transconjugant MOG101(pMOG686). As shown in EXAMPLE 5 the CBP encoded by pMOG686 is indeed targeted extracellularly. Similarly as described above a pMOG686 derived binary plasmid was constructed which contains in addition to the modified CBP gene a modified tobacco basic β-1,3-glucanase gene encoding an extracellularly targeted protein (described in more detail in EP-A 440 304 A1). The binary vector thus obtained was called pMOG688 and the corresponding Agrobacterium transconjugant MOG101(pMOG688).

EXAMPLE 4

Transformation of Plants

The transformation of tomato (Lycoversicon esculentum cv. Moneymaker) with Agrobacterium strains MOG101 (pMOG685), MOG101(pMOG686), MOG101(pMOG687) and MOG101(pMOG688) was performed essentially according to the procedure described by McCormick et al. (1986, Plant Cell Rep. 5, 81–84). For the transformation of tobacco use is made of the leaf-disc dip method (1985, Horsch et al., Science 227, 1229–1231). Leaf-discs were cocultivated with Aarobacterium strains MOG101 (pMOG685), MOG101(pMOG686), MOG101(pMOG687) or MOG101(pMOG688), and subsequently grown on selection medium with 100 mg/ml kanamycin. The transgenic shoots were regenerated into whole plants and analyzed for expression of the newly introduced genes. For this analysis use was made of the so-called Western blotting technique, using antibodies raised against either pathogenesis-related protein PR-4 (detection of CBP) or the tobacco basic β-1, 3-glucanase protein. In addition the Northern blotting technique was performed using the CBP cDNA and the basic β-1,3-glucanase gene as a probe. The Western blot analysis revealed no difference in mobility between CBP encoded by pMOG685 and CBP encoded by pMOG686, although the CBP coding regions in the two constructs differ 13 codons in length. This result suggests that in the plant wild-type CBP is C-terminally processed.

Further protein analysis has revealed that wild-type CBP is indeed C-terminally processed between Asn-residue 197 and Met-residue 198; this means that the modified CBP encoded by pMOG686 is 2 amino acids shorter than the wild-type processed CBP. This minor difference was found to have no adverse effects on the antifungal property of CBP.

EXAMPLE 5

Analysis of PMOG685- and pMOG686-Transgenic Tobacco Plants for Targeting of the Transgene Product.

In order to demonstrate extracellular targeting of CBP in pMOG686 transgenic tobacco plants, the following experiment was carried out. Leaves of F1 plants from pMOG685-transgenic plant lines and from pMOG6864-transgenic plant lines, and leaves of non-transgenic plants were used for the extraction of total proteins and of extracellular proteins. The extracellular fluid (EF) of these plants was collected according to the procedure described by De Wit and Spikman (1982, Physiol. Plant Pathol. 20, 1–11). After isolation of the EF, proteins were extracted as well from the remaining leaf material, so called "minus EF" fraction (–EF). For the analysis of proteins in the total extracts (Total), in the EF and in extracts of leaves from which the EF was removed (–EF), use was made of the Western blotting technique, using CBP specific antibodies, or antibodies raised against tomato P2 protein, or antibodies raised against tobacco PR-4. The results shown in Table 3 indicate that with the pMOG686-transgenic plants CBP is indeed targeted extracellularly.

TABLE 3

Targeting of CBP to the extracellular space in pM0G686 -transgenic tobacco plants.

| PLANT | PROTEIN SAMPLE | | |
|---|---|---|---|
| | TOTAL | EF | –EF |
| Non-transgenic | – | – | – |
| pMOG685 (unmodified) | ++++ | – | ++++ |
| pMOG686 (modified) | ++++ | +++ | + |

–: no CBP: + to ++++: increasing amounts of CBP.

Previously it was demonstrated that removal of a carboxyl-terminal propeptide of 22 amino acids from the tobacco basic β-1,3-glucanase protein results in efficient extracellular targeting of this protein in transgenic plants.

EXAMPLE 6

Analysis of Fungal Resistance in Transgenic Tobacco Plants

With the aid of Agrobacterium tumefaciens different transgenic tobacco plants were obtained that express the chimeric gene constructs delivered from the binary plasmids pMOG685, pMOG686, pMOG687 and pMOG688. Transgenic tobacco plants displaying good expression of the transgenes were analyzed for resistance to *Rhizoctonia solani*.

The soil-born phytopathogen *Rhizoctonia solani* causes disease symptoms on roots (root-rot) and stems (stem-canker) of a wide range of plant species, including tobacco. Infection of tobacco produces necrosis that reduces the ability of plants to collect and transport nutrients, which results in significant reductions in growth and biomass. Plant growth is correlated with the degree of fungal infection (1992, Logemann et al., Bio/technology, 10; 305–308). To assess the fungal resistance of transgenic tobacco plants were tested essentially according to the procedure described by Jach et al. (1992, Biopractice 1; 33–40) the following experiment was performed. Ten transgenic plants transformed with the vector pMOG23 (vector-transgenic plants), pMOG685, pMOG686, pMOG687 or pMOG688, and ten non-transgenic plants, all about 2 cm in size (four leaf stage), were grown in soil infested with *R.solani* (2 gr mycelium per liter soil) under 70%–90% relative humidity at 25° C. Subsequently, the growth increase (plant height) of the plant is monitored in time and is shown in Table 4. After 14 days the control plants (non-transgenic and vector-transgenic plants) are strongly retarded in growth compared to plants which were grown in non-infected soil. The pMOG685- and pMOG686-transgenic plants show a slightly enhanced resistance against *R.solani* as the growth of these plants is less retarded compared to the control plants. However, a better protection was observed in pMOG687- and pMOG688- transgenic plants, which illustrates the synergistic effect of CBP and basic β-1,3-glucanase against *R.solani*.

TABLE 4

*Rhizoctonia solani* assay on transgenic tobacco plants expressing either CBP or simultaneously CBP and basic β-1,3-glucanase.

| PLANT | Average Size Increase (cm)[a] (SD) |
|---|---|
| Non-transgenic | 5.2 |
| PMOG23 (vector) | 4.3 |
| pMOG685 | 6.3 |
| pMOG686 | 6.9 |
| pMOG687 | 15.0 |
| pMOG688 | 17.1 |

[a]Mean value is given of ten plants scored at day 14 post inoculation. Standard deviation in the range of 2 to 3 cm

EXAMPLE 7

Analysis of Fungal Resistance in Transgenic Tomato Plants

The fungus Fusarium oxysporum f.sp. lycopersici is a pathogen of the tomato plant causing complete wilting of the leaves, affection of the stem and eventually death of the plant. To test the susceptibility of tomato plants transformed with pMOG23, pMOG685, pMOG686, pMOG687, and pMOG688. Thirty of the best transgene expressors were tested with *Fusarium oxysporum* f.sp. lycopersici in three randomized blocks (10 plants/block). The roots of three weeks old plants were inoculated with a spore suspension of *F.oxysporum* f.sp. lycopersici fysio 1 (106 spores/ml) and were continued to grow in soil at 18° C. The disease symptoms are scored 21 days after infection of the plant. On a scale of 0 to 9 the plants are classified according to the infection grade of the vascular tissue and also the degree of wilting of the plant. In Table 5 estimations are given of the results.

TABLE 5

*Fusarium oxysporum* f.sp. *lycopersici* assay on transgenic tomato plants expressing either CBP or simultaneously CBP and basic β-1,3-glucanase.

| PLANT | Score[a] |
|---|---|
| Non-transgenic | 6.3 |
| PMOG23 (vector) | 6.5 |
| pMOG685 | 5.6 |
| pMOG686 | 5.1 |
| pMOG687 | 2.0 |
| pMOG688 | 1.7 |

[a]mean score of thirty plants at day 21 post inoculation. Scale: 0–9; 0: no infection; 9 heavily infected vascular system & plant death.

This example shows that tomato plants constitutively expressing either a wild-type CBP gene or a carboxyl terminal mutant CBP gene exhibit a slightly reduced susceptibility to the fungus *Fusarium oxysporum* f.sp. lycopersici, a natural pathogen of tomato plants. The results from Table 5 show, that an enhanced antifungal effect is present if CBP is targeted to the extracellular space (pMOG686-transgenic plants), as compared to the intracellularly localized CBP in pMOG685-transgenic plants. A synergistic effect of CBP and intracellular glucanase (Glu-I) was observed against *Fusarium oxysporum* f.sp. lycopersici in transgenic tomato plants expressing both genes constitutively. The control plants (non-transgenic and vector-transgenic plants) showed after 3 weeks severe disease symptoms, i.e. wilting, and were dead after five weeks. However, the pMOG687-transgenic plants and pMOG688-transgenic plants were strongly delayed in disease symptoms and show a strongly reduced susceptibility to *Fusarium oxysporum*.

We claim:

1. A chimeric gene comprising a polynucleotide sequence and a heterologous promoter, said polynucleotide sequence encoding an antifungal chitin binding protein that is obtainable from a plant, has a molecular weight in the range of 15 to 25 kDa, has a synergistic antifungal activity in combination with intracellular 1,3-β-glucanases, a low chitinase activity, and reacts with antisera that recognize a chitin binding protein occurring naturally in tobacco, said polynucleotide sequence being under the control of the heterologous promoter, wherein said polynucleotide hybridizes under stringent conditions to the complement of a DNA sequence selected from the group consisting of SEQ ID NO: 7, SEQ ID NO: 9 and SEQ ID NO: 13.

2. A chimeric gene as claimed in claim 1, said polynucleotide sequence having a DNA sequence selected from the group consisting of SEQ ID NO: 7, SEQ ID NO: 9, and SEQ ID NO: 13.

3. A chimeric gene according to claim 1
wherein the heterologous promoter is functional in a plant cell and the chimeric gene further comprises a transcriptional termination sequence that is functional in a plant cell.

4. A chimeric gene according to claim 3, wherein the heterologous promoter is obtainable from the CaMV 35S promoter.

5. A plasmid which comprises the chimeric gene according to claim 1 and which is suitable for cloning in a microorganism.

6. A plasmid which comprises the chimeric gene according to claim 1 and which is suitable for the transformation of plant material.

7. A microorganism containing a plasmid according to claim 5.

8. An Agrobacterium strain containing the plasmid of claim 6.

9. A method for obtaining a plant host which contains a chimeric plant expressible antifungal chitin binding protein gene comprising the steps of:

(1) introducing into a recipient cell of said plant host the chimeric gene of claim 1 and a selectable marker gene that is functional in said plant host, and (2) generating a plant from the recipient cell under conditions that allow for selection for the presence of the selectable marker gene.

10. A process according to claim 9, wherein the plant selectable marker gene is a gene conferring kanamycin resistance.

11. A recombinant plant DNA genome which contains a chimeric gene according to claim 1.

12. A recarbinant plant DNA genome according to claim 11, which further comprises a chimeric plant expressible 1,3-β-glucanase gene.

13. A plant cell or plant protoplast, which has a recombinant plant DNA genome according to claim 11.

14. A plant or a part thereof, containing a cell according to claim 13.

15. A plant or a part thereof, having a recombinant plant DNA genome according to claim 11.

16. A plant according to claim 15 which has reduced susceptibility to fungal infection.

17. A method for breeding a plant variety which has reduced susceptibility to fungi, comprising breeding the plant variety with at least one parental line of the plant variety having a recombinant DNA genome according to claim 11.

18. A method for reducing damage to agricultural crop plants as a result of fungal infection, comprising growing a plant according to claim 16.

19. A chimeric gene as claimed in claim 1 wherein the antifungal chitin binding protein encoded by said polynucleotide sequence has a chitinase activity which is less than 5% of the activity of class-I chitinases obtainable from tobacco.

20. A chimeric gene as in claim 1, wherein the chitinase activity of the antifungal chitin binding protein encoded by said polynucleotide sequence is less than 10% of the activity of class-I chitinases obtainable from tobacco.

21. A chimeric gene comprising a polynucleotide sequence and a heterologous promoter, wherein said heterologous promoter does not naturally promote expression of said polynucleotide sequence, and wherein the polynucleotide sequence encodes an antifungal chitin binding protein that is obtainable from tobacco, has a molecular weight of about 20 kDa, shows a synergistic antifungal activity in combination with intracellular 1,3-β-glucanase from tobacco and has less than 5% of the chitinase activity of tobacco class-I chitinase.

22. A chimeric gene as claimed in claim 19 wherein the antifungal chitin binding protein encoded by said polynucleotide sequence has substantially the amino acid sequence of SEQ ID NO: 8 or SEQ ID NO: 10, or a portion of said amino acid sequence.

23. A substantially pure polynucleotide sequence encoding an antifungal chitin binding protein from a tobacco plant, said antifungal chitin binding protein having a molecular weight in the range of 15 to 25 kDa, a synergistic antifungal activity in combination with intracellular 1,3-β-glucanases and low chitinase activity, said antifungal chitin binding protein reacting with antisera that recognize a chitin binding protein occurring naturally in tobacco.

24. A method for reducing susceptibility of a plant or progeny of the plant to fungi comprising transforming the plant with the chimeric gene of claim 1.

25. A method for reducing susceptibility of a plant or progeny of the plant to fungi comprising (a) transforming the plant with a polynucleotide sequence that hybridizes under stringent conditions to the complement of a DNA sequence selected from the group consisting of SEQ ID NO: 7, SEQ ID NO: 9 and SEQ ID NO: 13 said polynucleotide sequence encoding an antifungal chitin binding protein that is obtainable from a plant, has a molecular weight in the range of 15 to 20 kDa, a synergistic antifungal activity in combination with intracellular 1,3-β-glucanases and low chitinase activity, said antifungal chitin binding protein reacting with antisera that recognize a chitin binding protein occurring naturally in tobacco, and (b) selecting a transformant having a reduced susceptibility to the fungi.

26. A method as claimed in claim 25, wherein the polynucleotide sequence is selected from the group consisting of SEQ ID NO: 7, SEQ ID NO: 9, and SEQ ID NO: 13.

27. A method as claimed in claim 25, further comprising transforming the plant or the plant progeny with a second polynucleotide sequence encoding a protein that has a synergistic antifungal activity in combination with said antifungal chitin binding protein.

28. A method as claimed in claim 27, wherein the second polynucleotide encodes an intracellular β-1,3-glucanase.

29. A method as claimed in claim 25, wherein the polynucleotide sequence also encodes a second protein that has a synergistic antifungal activity in combination with said antifungal chitin binding protein, said polynucleotide sequence causing expression in the plant or plant progeny of the antifungal chitin binding protein and the second protein.

30. A method as claimed according to claim 29, wherein the second protein is an intracellular β-1,3-glucanase.

31. A method for obtaining a plant host which contains a chimeric expressible antifungal chitin binding protein gene comprising the steps of:

(1) introducing into a recipient cell of said plant host a chimeric gene according to claim 1, and (2) generating a plant from said recipient cell.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
            (A) LENGTH: 15 Amino Acids
            (B) TYPE: Amino Acid
            (D) TOPOLOGY: Linear (ii) MOLECULE TYPE: Protein (iii) HYPOTHETICAL: No (v) FRAGMENT TYPE: Internal (vi) ORIGINAL SOURCE:
            (A) ORGANISM: Nicotiana tabacum
            (B) STRAIN: Samsun NN
            (D) DEVELOPMENTAL STAGE: Mature
            (F) TISSUE TYPE: Leaf, wounded (xi) SEQUENCE DESCRIPTION: SEQ ID NO:1:

Trp Thr Ala Phe Xaa Gly Pro Val Gly Pro Xaa Gly Arg Asp Ser
 1               5                  10                  15

(2) INFORMATION FOR SEQ ID NO:2:

(i) SEQUENCE CHARACTERISTICS:
            (A) LENGTH: 30 Amino Acids
            (B) TYPE: Amino Acid
            (D) TOPOLOGY: Linear (ii) MOLECULE TYPE: Protein (iii) HYPOTHETICAL: NO (v) FRAGMENT TYPE: Internal (vi) ORIGINAL SOURCE:
            (A) ORGANISM: Nicotiana tabacum
            (B) STRAIN: Samsun NN
            (D) DEVELOPMENTAL STAGE: Mature
            (F) TISSUE TYPE: Leaf, wounded (xi) SEQUENCE DESCRIPTION: SEQ ID NO:2:

Glu Tyr Xaa Ser Pro Ser Gln Gly Xaa Gln Ser Gln Xaa Ser Gly Gly
 1               5                  10                  15

Gly Gly Xaa Gly Gly Gly Gly Gly Gly Gly Ala Gln Asn
            20                  25                  30

(2) INFORMATION FOR SEQ ID NO:3:

(i) SEQUENCE CHARACTERISTICS:
            (A) LENGTH: 20 Base Pairs
            (B) TYPE: Nucleic Acid
            (C) STRANDEDNESS: Single
            (D) TOPOLOGY: Linear (ii) MOLECULE TYPE: cDNA (iii) HYPOTHETICAL: YES (ix) FEATURE:
            (A) NAME/KEY: misc_feature
            (B) LOCATION: 1..20
            (D) OTHER INFORMATION: /label= synthetic (xi) SEQUENCE DESCRIPTION: SEQ ID NO:3:

CAGCTATGAC CATGATTACG                                                    20

(2) INFORMATION FOR SEQ ID NO:4:

(i) SEQUENCE CHARACTERISTICS:
            (A) LENGTH: 38 Base Pairs
            (B) TYPE: Nucleic Acid
            (C) STRANDEDNESS: Single (D) TOPOLOGY: Linear (ii) MOLECULE TYPE: cDNA to mRNA (iii) HYPOTHETICAL: YES (ix) FEATURE:
        (A) NAME/KEY: misc_feature
        (B) LOCATION: 1..38
        (D) OTHER INFORMATION: /label= synthetic (xi) SEQUENCE DESCRIPTION: SEQ ID NO:4:

CTCGAATTCG GWCCNACNGG WCCRTARAAA GCNGTCCA                                38

(2) INFORMATION FOR SEQ ID NO:5:

(i) SEQUENCE CHARACTERISTICS:
        (A) LENGTH: 30 Base Pairs
        (B) TYPE: Nucleic Acid
        (C) STRANDEDNESS: Single
        (D) TOPOLOGY: Linear (ii) MOLECULE TYPE: cDNA to mRNA (iii) HYPOTHETICAL: YES (ix) FEATURE:
        (A) NAME/KEY: misc_feature
        (B) LOCATION: 1..30
        (D) OTHER INFORMATION: /label= synthetic (xi) SEQUENCE DESCRIPTION: SEQ ID NO:5:

CTCGAATTCG GCACGAGGAT CCTCTATTTC                                        30

(2) INFORMATION FOR SEQ ID NO:6:

(i) SEQUENCE CHARACTERISTICS:
        (A) LENGTH: 30 Base Pairs
        (B) TYPE: Nucleic Acid
        (C) STRANDEDNESS: Single
        (D) TOPOLOGY: Linear (ii) MOLECULE TYPE: cDNA to mRNA (iii) HYPOTHETICAL: YES (ix) FEATURE:
        (A) NAME/KEY: misc_feature
        (B) LOCATION: 1..30
        (D) OTHER INFORMATION: /label= synthetic (xi) SEQUENCE DESCRIPTION: SEQ ID NO:6:

CTCGAATTCC ACTGCACTGG CTTTGGCAGC                                        30

(2) INFORMATION FOR SEQ ID NO:7:

(i) SEQUENCE CHARACTERISTICS:
        (A) LENGTH: 889 Base Pairs
        (B) TYPE: Nucleic Acid
        (C) STRANDEDNESS: Single
        (D) TOPOLOGY: Linear (ii) MOLECULE TYPE: cDNA to mRNA (iii) HYPOTHETICAL: NO (iv) ANTI-SENSE: NO (vi) ORIGINAL SOURCE:
        (A) ORGANISM: Nicotiana tabacum
        (B) STRAIN: Samsun NN
        (D) DEVELOPMENTAL STAGE: Mature
        (F) TISSUE TYPE: Leaf, wounded (vii) IMMEDIATE SOURCE:
    (A) LIBRARY: lambda zap
    (B) CLONE: CBP4.4

(ix) FEATURE:
    (A) NAME/KEY: CDS
    (B) LOCATION: 16..639

(ix) FEATURE:
    (A) NAME/KEY: misc_feature
    (B) LOCATION: 1..14

(ix) FEATURE:
    (A) NAME/KEY: misc_feature
    (B) LOCATION: 866..889
    (D) OTHER INFORMATION: /function= "XhoI-linker"

(xi) SEQUENCE DESCRIPTION: SEQ ID NO:7:

```
GAATTCGGCA CGAGG GGA AAG CTA AGT ACT CTT TTG CTT GTT CTG ATC CTC         51
                Gly Lys Leu Ser Thr Leu Leu Leu Val Leu Ile Leu
                  1               5                      10

TAT TTC ATA GCC GCA GGT GCC AAC GCA CAG CAG TGC GGA AGG CAA AGG          99
Tyr Phe Ile Ala Ala Gly Ala Asn Ala Gln Gln Cys Gly Arg Gln Arg
             15                  20                  25

GGA GGA GCC TTA TGC AGT GGA AAC TTG TGC TGC AGC CAA TTT GGG TGG         147
Gly Gly Ala Leu Cys Ser Gly Asn Leu Cys Cys Ser Gln Phe Gly Trp
         30                  35                  40

TGT GGG TCT ACA CCG GAA TAC TGT TCT CCT AGC CAA GGC TGC CAA AGC         195
Cys Gly Ser Thr Pro Glu Tyr Cys Ser Pro Ser Gln Gly Cys Gln Ser
 45                  50                  55                  60

CAG TGC AGT GGC GGC GGA GGC GGT GGA GGT GGC GGT GGT GGT GGT             243
Gln Cys Ser Gly Gly Gly Gly Gly Gly Gly Gly Gly Gly Gly Gly
                 65                  70                  75

GCG CAA AAC GTT AGG GCA ACA TAT CAT ATA TAT AAC CCG CAG AAT GTT         291
Ala Gln Asn Val Arg Ala Thr Tyr His Ile Tyr Asn Pro Gln Asn Val
             80                  85                  90

GGG TGG GAT TTG TAT GCA GTT AGT GCG TAC TGC TCA ACT TGG GAT GGT         339
Gly Trp Asp Leu Tyr Ala Val Ser Ala Tyr Cys Ser Thr Trp Asp Gly
         95                  100                 105

AAC AAG CCT TTG GCA TGG CGG AGG AAG TAT GGT TGG ACT GCA TTC TGT         387
Asn Lys Pro Leu Ala Trp Arg Arg Lys Tyr Gly Trp Thr Ala Phe Cys
     110                 115                 120

GGC CCT GTT GGA CCT CGT GGC CGA GAC TCT TGT GGC AAA TGC TTA AGG         435
Gly Pro Val Gly Pro Arg Gly Arg Asp Ser Cys Gly Lys Cys Leu Arg
125                 130                 135                 140

GTG ACA AAT ACA GGC ACA GGA GCT CAG ACC ACA GTG AGA ATC GTG GAT         483
Val Thr Asn Thr Gly Thr Gly Ala Gln Thr Thr Val Arg Ile Val Asp
                 145                 150                 155

CAA TGC AGC AAT GGC GGA CTA GAC TTG GAC GTT AAT GTT TTC CGG CAG         531
Gln Cys Ser Asn Gly Gly Leu Asp Leu Asp Val Asn Val Phe Arg Gln
         160                 165                 170

CTC GAC ACA GAC GGA AGA GGG AAT CAA CGC GGC CAT CTT ATT GTG AAC         579
Leu Asp Thr Asp Gly Arg Gly Asn Gln Arg Gly His Leu Ile Val Asn
     175                 180                 185

TAC GAG TTT GTT AAT TGT GGT GAC AAT ATG AAT GTT CTG CTA TCC CCA         627
Tyr Glu Phe Val Asn Cys Gly Asp Asn Met Asn Val Leu Leu Ser Pro
 190                 195                 200

GTT GAC AAA GAA TAAGAAGCCA TCGATGCCCA TGTTTTAGTC TTTGACGGCC             679
Val Asp Lys Glu
205

CAAATAAAAG TAAAGAACG ATATGTAAAA GGAAAAAGAA AATAAAGTTG CTTTGAAGGG         739

TTAGGCAATT CCAATTTCTA TATAAGAATG TCTTTCGTTT GGGAATAATG AGGTGACGTG       799

TGTATGCGAA TATTGTGATT TTAAATAAAG AATCGCAGTG GGACAGTATT TGTTGGTCTC       859
```

ATTCCGAAAA AAAAAAAAAA AAAACTCGAG                                          889

(2) INFORMATION FOR SEQ ID NO:8:

(i) SEQUENCE CHARACTERISTICS:
        (A) LENGTH: 208 Amino Acids
        (B) TYPE: Amino Acid
        (D) TOPOLOGY: Linear (ii) MOLECULE TYPE: protein (xi) SEQUENCE DESCRIPTION: SEQ ID NO:8:

Gly Lys Leu Ser Thr Leu Leu Val Leu Ile Leu Tyr Phe Ile Ala
 1               5                  10                  15

Ala Gly Ala Asn Ala Gln Gln Cys Gly Arg Gln Arg Gly Gly Ala Leu
                20                  25                  30

Cys Ser Gly Asn Leu Cys Cys Ser Gln Phe Gly Trp Cys Gly Ser Thr
            35                  40                  45

Pro Glu Tyr Cys Ser Pro Ser Gln Gly Cys Gln Ser Gln Cys Ser Gly
     50                  55                  60

Gly Gly Gly Gly Gly Gly Gly Gly Gly Ala Gln Asn Val
65                  70                  75                  80

Arg Ala Thr Tyr His Ile Tyr Asn Pro Gln Asn Val Gly Trp Asp Leu
                85                  90                  95

Tyr Ala Val Ser Ala Tyr Cys Ser Thr Trp Asp Gly Asn Lys Pro Leu
                100                 105                 110

Ala Trp Arg Arg Lys Tyr Gly Trp Thr Ala Phe Cys Gly Pro Val Gly
                115                 120                 125

Pro Arg Gly Arg Asp Ser Cys Gly Lys Cys Leu Arg Val Thr Asn Thr
    130                 135                 140

Gly Thr Gly Ala Gln Thr Thr Val Arg Ile Val Asp Gln Cys Ser Asn
145                 150                 155                 160

Gly Gly Leu Asp Leu Asp Val Asn Val Phe Arg Gln Leu Asp Thr Asp
                165                 170                 175

Gly Arg Gly Asn Gln Arg Gly His Leu Ile Val Asn Tyr Glu Phe Val
                180                 185                 190

Asn Cys Gly Asp Asn Met Asn Val Leu Leu Ser Pro Val Asp Lys Glu
                195                 200                 205

(2) INFORMATION FOR SEQ ID NO:9:

(i) SEQUENCE CHARACTERISTICS:
        (A) LENGTH: 764 Base Pairs
        (B) TYPE: Nucleic Acid
        (C) STRANDEDNESS: Single
        (D) TOPOLOGY: Linear (ii) MOLECULE TYPE: cDNA to mRNA (iii) HYPOTHETICAL: NO (vi) ORIGINAL SOURCE:
        (A) ORGANISM: Nicotiana tabacum
        (B) STRAIN: Samsun NN
        (D) DEVELOPMENTAL STAGE: Mature
        (F) TISSUE TYPE: Leaf, wounded (vii) IMMEDIATE SOURCE:
        (A) LIBRARY: lambda zap
        (B) CLONE: CBP5.2

(ix) FEATURE:
        (A) NAME/KEY: misc_feature
        (B) LOCATION: 1..14

(D) OTHER INFORMATION: /function= "EcoRI-linker"

(ix) FEATURE:
    (A) NAME/KEY: CDS
    (B) LOCATION: 42..674
    (D) OTHER INFORMATION: /product= "chitin binding protein"

(ix) FEATURE:
    (A) NAME/KEY: misc_feature
    (B) LOCATION: 741..764
    (D) OTHER INFORMATION: /function= "XhoI-linker"

(xi) SEQUENCE DESCRIPTION: SEQ ID NO:9:

```
GAATTCGGCA CGAGACAACA CCAGTTCAAA CACTTTGAAA A ATG GGA AAG CTA           53
                                              Met Gly Lys Leu
                                                1

AGT ACA CTT TTA TTT GCT CTG GTC CTC TAT GTC ATA GCC GCA GGA GCT        101
Ser Thr Leu Leu Phe Ala Leu Val Leu Tyr Val Ile Ala Ala Gly Ala
  5                  10                  15                  20

AAT GCA CAG CAG TGC GGC AGG CAA AGG GGA GGA GCC TTA TGC AGT GGA        149
Asn Ala Gln Gln Cys Gly Arg Gln Arg Gly Gly Ala Leu Cys Ser Gly
                 25                  30                  35

AAC TTG TGC TGC AGT CAA TTT GGG TGG TGT GGG TCT ACA CCA GAA TAC        197
Asn Leu Cys Cys Ser Gln Phe Gly Trp Cys Gly Ser Thr Pro Glu Tyr
             40                  45                  50

TGT TCT CCT AGC CAA GGC TGC CAA AGC CAG TGC AGT GGC GGT GGA GGC        245
Cys Ser Pro Ser Gln Gly Cys Gln Ser Gln Cys Ser Gly Gly Gly Gly
         55                  60                  65

GGC GGT GGA GGT GGC GGC GGA GGC GGG GGT GCT GCG CAA AAC GTT AGG        293
Gly Gly Gly Gly Gly Gly Gly Gly Gly Ala Ala Gln Asn Val Arg
     70                  75                  80

GCA ACA TAT CAT ATA TAT AAC CCG CAG AAT GTT GGG TGG GAT TTG TAT        341
Ala Thr Tyr His Ile Tyr Asn Pro Gln Asn Val Gly Trp Asp Leu Tyr
 85                  90                  95                 100

GCA GTT AGT GCG TAC TGC TCA ACT TGG GAT GGT AAC AAG CCT TTG GCA        389
Ala Val Ser Ala Tyr Cys Ser Thr Trp Asp Gly Asn Lys Pro Leu Ala
                105                 110                 115

TGG AGG AGG AAG TAT GGT TGG ACT GCA TTT TGT GGC CCT GTT GGA CCT        437
Trp Arg Arg Lys Tyr Gly Trp Thr Ala Phe Cys Gly Pro Val Gly Pro
            120                 125                 130

CGT GGC CGA GAC TCT TGT GGC AAA TGC TTA AGG GTG ACA AAT ACA GGC        485
Arg Gly Arg Asp Ser Cys Gly Lys Cys Leu Arg Val Thr Asn Thr Gly
        135                 140                 145

ACA GGA GCT CAG ACC ACA GTG AGA ATC GTG GAT CAA TGC AGC AAT GGC        533
Thr Gly Ala Gln Thr Thr Val Arg Ile Val Asp Gln Cys Ser Asn Gly
    150                 155                 160

GGA CTA GAC TTG GAC GTT AAC GTT TTC CGG CAG CTC GAC ACA GAC GGA        581
Gly Leu Asp Leu Asp Val Asn Val Phe Arg Gln Leu Asp Thr Asp Gly
165                 170                 175                 180

AGA GGG AAT CAA CGT GGC CAC CTT ATT GTG AAC TAC GAG TTT GTT AAT        629
Arg Gly Asn Gln Arg Gly His Leu Ile Val Asn Tyr Glu Phe Val Asn
                185                 190                 195

TGT GGT GAC AAT ATG AAT GTT CTG GTA TCC CCA GTT GAC AAG GAA            674
Cys Gly Asp Asn Met Asn Val Leu Val Ser Pro Val Asp Lys Glu
            200                 205                 210

TAAGAAGCTA TATATGGCCA TGTTTAGTCT TTGACGGCCC AAATAAAGT AAAAAGAACG       734

ATATGTAAAA AAAAAAAAAA AAAACTCGAG                                       764
```

(2) INFORMATION FOR SEQ ID NO:10:

(i) SEQUENCE CHARACTERISTICS:
        (A) LENGTH: 211 Amino Acids
        (B) TYPE: Amino Acid (D) TOPOLOGY: Linear (ii) MOLECULE TYPE: protein (xi) SEQUENCE DESCRIPTION: SEQ ID NO:10:

```
Met Gly Lys Leu Ser Thr Leu Leu Phe Ala Leu Val Leu Tyr Val Ile
 1               5                  10                  15
Ala Ala Gly Ala Asn Ala Gln Gln Cys Gly Arg Gln Arg Gly Gly Ala
                20                  25                  30
Leu Cys Ser Gly Asn Leu Cys Cys Ser Gln Phe Gly Trp Cys Gly Ser
                35                  40                  45
Thr Pro Glu Tyr Cys Ser Pro Ser Gln Gly Cys Gln Ser Gln Cys Ser
 50                  55                  60
Gly Gly Gly Gly Gly Gly Gly Gly Gly Gly Gly Gly Gly Gly Ala Ala
 65                  70                  75                  80
Gln Asn Val Arg Ala Thr Tyr His Ile Tyr Asn Pro Gln Asn Val Gly
                85                  90                  95
Trp Asp Leu Tyr Ala Val Ser Ala Tyr Cys Ser Thr Trp Asp Gly Asn
                100                 105                 110
Lys Pro Leu Ala Trp Arg Arg Lys Tyr Gly Trp Thr Ala Phe Cys Gly
                115                 120                 125
Pro Val Gly Pro Arg Gly Arg Asp Ser Cys Gly Lys Cys Leu Arg Val
130                 135                 140
Thr Asn Thr Gly Thr Gly Ala Gln Thr Thr Val Arg Ile Val Asp Gln
145                 150                 155                 160
Cys Ser Asn Gly Gly Leu Asp Leu Asp Val Asn Val Phe Arg Gln Leu
                165                 170                 175
Asp Thr Asp Gly Arg Gly Asn Gln Arg Gly His Leu Ile Val Asn Tyr
                180                 185                 190
Glu Phe Val Asn Cys Gly Asp Asn Met Asn Val Leu Val Ser Pro Val
                195                 200                 205
Asp Lys Glu
    210
```

(2) INFORMATION FOR SEQ ID NO:11:

(i) SEQUENCE CHARACTERISTICS:
        (A) LENGTH: 53 Base Pairs
        (B) TYPE: Nucleic Acid
        (C) STRANDEDNESS: Single
        (D) TOPOLOGY: Linear (ii) MOLECULE TYPE: cDNA to mRNA (iii) HYPOTHETICAL: YES (ix) FEATURE:
        (A) NAME/KEY: misc_feature
        (B) LOCATION: 1..53
        (D) OTHER INFORMATION: /label= synthetic (xi) SEQUENCE DESCRIPTION: SEQ ID NO:11:

CGCGGATCCA ACACCAGTTC AAACACTTTG AAAAATGGGA AAGCTAAGTA CTC      53

(2) INFORMATION FOR SEQ ID NO:12:

(i) SEQUENCE CHARACTERISTICS:
        (A) LENGTH: 29 Base Pairs
        (B) TYPE: Nucleic Acid
        (C) STRANDEDNESS: Single
        (D) TOPOLOGY: Linear (ii) MOLECULE TYPE: cDNA to mRNA -continued

```
    (iii) HYPOTHETICAL: YES (ix) FEATURE:
         (A) NAME/KEY: misc_feature
         (B) LOCATION: 1..29
         (D) OTHER INFORMATION: /label= synthetic (xi) SEQUENCE DESCRIPTION: SEQ ID NO:12:

GCGGGATCCG GAATGAGACC AACAAATAC                                              29

(2) INFORMATION FOR SEQ ID NO:13:

(i) SEQUENCE CHARACTERISTICS:
         (A) LENGTH: 889 Base Pairs
         (B) TYPE: Nucleic Acid
         (C) STRANDEDNESS: double
         (D) TOPOLOGY: Linear (ii) MOLECULE TYPE: cDNA to mRNA (iii) HYPOTHETICAL: YES (iv) ANTI-SENSE: NO (vi) ORIGINAL SOURCE:
         (A) ORGANISM: Nicotiana tabacum
         (B) STRAIN: Samsun NN
         (F) TISSUE TYPE: Leaf, wounded (vii) IMMEDIATE SOURCE:
         (B) CLONE: CBP4.4T (xi) SEQUENCE DESCRIPTION: SEQ ID NO:13:

GGATCCAACA CCAGTTCAAA CACTTTGAAA AATGGGAAAG CTAAGTACTC TTTTGCTTGT      60

TCTGATCCTC TATTTCATAG CCGCAGGTGC CAACGCACAG CAGTGCGGAA GGCAAAGGGG     120

AGGAGCCTTA TGCAGTGGAA ACTTGTGCTG CAGCCAATTT GGGTGGTGTG GGTCTACACC     180

GGAATACTGT TCTCCTAGCC AAGGCTGCCA AAGCCAGTGC AGTGGCGGCG GAGGCGGCGG     240

TGGAGGTGGC GGTGGTGGTG GTGCGCAAAA CGTTAGGGCA ACATATCATA TATATAACCC     300

GCAGAATGTT GGGTGGGATT TGTATGCAGT TAGTGCGTAC TGCTCAACTT GGGATGGTAA     360

CAAGCCTTTG GCATGGCGGA GGAAGTATGG TTGGACTGCA TTCTGTGGCC CTGTTGGACC     420

TCGTGGCCGA GACTCTTGTG GCAAATGCTT AAGGGTGACA AATACAGGCA CAGGAGCTCA     480

GACCACAGTG AGAATCGTGG ATCAATGCAG CAATGGCGGA CTAGACTTGG ACGTTAATGT     540

TTTCCGGCAG CTCGACACAG ACGGAAGAGG GAATCAACGC GGCCATCTTA TTGTGAACTA     600

CGAGTTTGTT AATTGTGGTG ACAATATGAA TGTTCTGCTA TCCCCAGTTG ACAAAGAATA     660

AGAAGCCATC GATGCCCATG TTTTAGTCTT TGACGGCCCA AATAAAAGTA AAAGAACGAT     720

ATGTAAAAGG AAAAAGAAAA TAAAGTTGCT TTGAAGGGTT AGGCAATTCC AATTTCTATA     780

TAAGAATGTC TTTCGTTTGG GAATAATGAG GTGACGTGTG TATGCAATA TTGTGATTTT      840

AAATAAAGAA TCGCAGTGGG ACAGTATTTG TTGGTCTCAT TCCGGATCC                 889
```